(12) United States Patent
Koppes et al.

(10) Patent No.: US 6,602,366 B2
(45) Date of Patent: Aug. 5, 2003

(54) TRIAZOLYL-TETRAZINYL-AMINOTRIAZINE COMPOUNDS USEFUL IN PYROTECHNIC COMPOSITIONS AND PROCESS THEREOF

(75) Inventors: William M. Koppes, Adelphi, MD (US); Michael E. Sitzmann, Adelphi, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/171,134

(22) Filed: Jun. 14, 2002

(65) Prior Publication Data

US 2003/0013877 A1 Jan. 16, 2003

Related U.S. Application Data

(63) Continuation-in-part of application No. 09/874,946, filed on Jun. 6, 2001, now Pat. No. 6,423,844.

(51) Int. Cl.[7] .................... C07D 487/14; C06B 45/10; C06C 15/00
(52) U.S. Cl. .................... 149/56; 149/76; 149/119; 544/179
(58) Field of Search .................... 544/179; 149/56, 149/76, 119

(56) References Cited

U.S. PATENT DOCUMENTS

| 2,473,797 | A | 6/1949 | Kaiser et al. | 260/249.5 |
|---|---|---|---|---|
| 2,475,440 | A | 7/1949 | Walter | 260/239 |
| 3,061,605 | A | 10/1962 | D'Alelio | 260/239.7 |
| 3,939,084 | A | 2/1976 | Sullivan | 252/47.5 |
| 4,517,182 | A | 5/1985 | Cheng | 514/413 |
| 4,549,018 | A | 10/1985 | Siedle | 544/225 |
| 4,565,815 | A | 1/1986 | Kim et al. | 514/246 |
| 4,656,171 | A | 4/1987 | Austel et al. | 514/250 |
| 4,734,413 | A | 3/1988 | Wade | 514/222 |
| 4,954,498 | A | 9/1990 | Mertens et al. | 514/254 |
| 5,173,492 | A | 12/1992 | Suzuki et al. | 514/267 |
| 5,246,932 | A | 9/1993 | Caulkett et al. | 514/245 |
| 5,260,291 | A | 11/1993 | Lunt et al. | 514/183 |
| 5,270,316 | A | 12/1993 | Suzuki et al. | 514/267 |
| 5,281,706 | A | 1/1994 | Coburn et al. | 544/179 |
| 5,677,309 | A | 10/1997 | Chen et al. | 514/267 |
| 5,682,014 | A | 10/1997 | Highsmith et al. | 149/36 |
| 5,789,407 | A | 8/1998 | Suzuki et al. | 514/246 |
| 5,792,766 | A | 8/1998 | Chen et al. | 514/243 |
| 5,869,659 | A | 2/1999 | Stolle et al. | 544/114 |
| 5,917,146 | A | 6/1999 | Hiskey et al. | 149/36 |
| 5,955,465 | A | 9/1999 | Chen et al. | 514/267 |
| 6,060,478 | A | 5/2000 | Gilligan et al. | 514/258 |
| 6,075,016 | A | 6/2000 | Chasin et al. | 514/183 |
| 6,103,731 | A | 8/2000 | Chen et al. | 514/267 |
| 6,214,139 | B1 | 4/2001 | Hiskey et al. | 149/36 |
| 6,297,252 | B1 | 10/2001 | Chen et al. | 514/267 |
| 6,312,537 | B1 | 11/2001 | Hiskey et al. | 149/36 |
| 6,313,124 | B1 | 11/2001 | He et al. | 514/246 |

OTHER PUBLICATIONS

Article: "The Synthesis and Dimeoth–Type Rearrangement of 5,7–Bis(dimethylamino)–3–(methylthio)–s–triazolo[4,3–a]–s–triazine", DeMilo et al., J. Heterocyclic Chem. 10, 231 (Apr. 1973), pp 231–233.

Article: "New Synthesis of Dyes of the Triazine", Series II. VAT Dyes of the Triazolo–Triazine Series by A. Titkov and I.D. Pletnev, Scientific Research Institute of Intermediates and Dyes, translated from Zhurnal Obshchel Khimil, vol. 33, No. 4, pp. 1355–1357, Apr. 1963.

Abstract: No. 93042a Basic azo dye. Maeda, Hhigeo et al. (40–Dyes, vol. 81, 1974), referencing Maeda et al. Japan Kokai 74 24,226.

Abstract: No. 122766x Basic azo dye. Maeda, Hhigeo et al. (40–Dyes, vol. 81, 1974), referencing Maeda et al. Japan Kokai 74 27,287.

Article: "Chemistry of Dicyandiamide V Structures of Guanazo–and Pyro–Guanazoles, and Reaction of Dicyandiamide with 3–Amino–5–Substituted–1,2,4,4 H–Triazoles", kaiser et al. J. Organic Chemistry, vol. 18, 1953, pp. 1610–1614.

*Primary Examiner*—Richard L. Raymond
*Assistant Examiner*—Venkataraman Balasubramanian
(74) *Attorney, Agent, or Firm*—Mark Homer

(57) ABSTRACT

Pyrotechnic compositions use a salt or complex of a triazolyl-tetrazinyl-aminotriazine compound. The general chemical structure of the triazolyl-tetrazinyl-aminotriazine is:

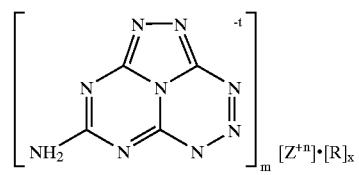

with values of the variables defined within the disclosure.

20 Claims, No Drawings

TRIAZOLYL-TETRAZINYL-AMINOTRIAZINE COMPOUNDS USEFUL IN PYROTECHNIC COMPOSITIONS AND PROCESS THEREOF

This application is a continuation-in-part (CIP) of U.S. patent application Ser. No. 09/874,946, entitled "Process for Making 1,2,4-Triazolo[4,3-a][1,3,5] Triazine-3,5,7-Triamine", filed Jun. 6, 2001, which is now U.S. Pat. No. 6,423,844 B1.

STATEMENT OF GOVERNMENT INTEREST

The invention described herein may be manufactured and used by or for the Government of the United States of America for governmental purposes without payment of any royalties thereon or therefor.

BACKGROUND OF THE INVENTION

1. Field of the Invention

The present invention pertains to novel high nitrogen content, low carbon content energetic compounds. More particularly, the present invention pertains to triazolyl-tetrazinyl-aminotriazine compounds, and complexes and salts thereof. The triazolyl-tetrazinyl-aminotriazine compounds, and their complexes and salts, of the present invention are particularly useful as energetic ingredients for use in pyrotechnics, most particularly smokeless pyrotechnics. The low-smoke pyrotechnic compositions of the present invention may include metal salts together with or added separately into the pyrotechnic composition.

2. Brief Description of the Related Art

Specialized events and amusement parks often exhibit fireworks. These fireworks result from pyrotechnic compositions generally employing a large variety of colorants. However, the smoke resulting from large quantities of burning pyrotechnics may become a nuisance for any spectators in the area, such as obstructing the view to the fireworks or irritating the eyes and throats of the people in the audience.

Fireworks generally employ an initial burst and a main burst mechanism. The main burst includes color-producing pellets, or "stars", which ignite during the main burst detonation to provide the light and color of a fireworks display. Firework composition have been described in such patents as U.S. Pat. No. 6,312,537 to Hiskey et al., entitled "Low-Smoke Pyrotechnic Compositions" which in part identifies a low-smoke pyrotechnic composition of dihydrazino-s-tetrazine, its derivatives and salts with an oxidizing agent and colorant. Hiskey et al. describes known colorants in pyrotechnics to include cupric oxide, barium nitrate, strontium nitrate and the like, as well as those described in U.S. Pat. No. 5,682,014 to Highsmith et al. The disclosures of these two patents are herein incorporated by reference.

It is an object of the present invention to provide novel triazolyl-tetrazinyl-aminotriazine compounds, and the complexes and salts thereof in pyrotechnic compositions, particularly low-smoke compositions used in fireworks.

SUMMARY OF THE INVENTION

The present invention includes a pyrotechnic composition comprising a compound having the chemical structure:

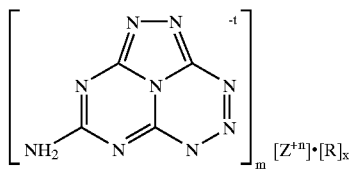

wherein $Z^+$ comprises $H^+$ or a cation; R comprises a complexing component; and m=1, 2 or 3; n=0, 1, 2 or 3; x=0, 1, 2 or 3; and t=0 or 1. The structure provides the complex and forms of triazolyl-tetrazinyl-aminotriazine.

The present invention also includes a method of making a pyrotechnic composition comprising a triazolyl-tetrazinyl-aminotriazine compound comprising the steps of providing a triazolyl-triaminotriazine precursor and diazotizing the precursor to form the triazolyl-tetrazinyl-aminotriazine, or derivative thereof.

The present invention further includes a pyrotechnic composition comprising a triazolyl-tetrazinyl-aminotriazine compound.

DETAILED DESCRIPTION OF THE INVENTION

The present invention includes novel triazolyl-tetrazinyl-aminotriazine compounds, and the complexes and salts thereof, that are particularly useful in pyrotechnic compositions with special applicability in fireworks compositions. The fireworks compositions of the present invention are characterized as low-smoke compositions and can be formulated to be essentially smoke-free. Low smoke compositions have decreasing amounts of residual smoke after pyrotechnic bum that are operationally and commercially useful. The triazolyl-tetrazinyl-aminotriazine compounds, and their complexes and salts, provide a high-nitrogen content, low-carbon content energetic material as a principal component within the pyrotechnic composition.

The present invention includes a pyrotechnic composition comprising a compound having the chemical structure:

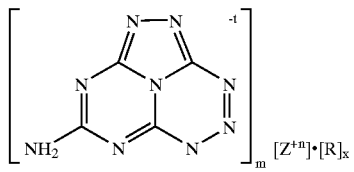

wherein $Z^+$ comprises $H^+$ or a cation; R comprises a complexing component; and m=1, 2 or 3; n=0, 1, 2 or 3; x=0, 1, 2 or 3; and t=0 or 1.

The complex form of the triazolyl-tetrazinyl-aminotriazine occurs when $Z^+$ comprises $H^+$, and the value of x is not 0. The complex form include the hydrogen attached to a nitrogen atom in the tetrazinyl ring (see e.g. Example 19B). Complexes of the present invention include, for example, R=Dihydrazino-s-tetrazine, Trihydrazino-s-triazine, 5-Aminotetrazole, N-aminotriazoles, and bis-(1(2) H-tetrazol-5-yl)-amine.

The pyrotechnic compositions herein include metal and non-metal triazolyl-tetrazinyl-aminotriazine compound salts. In one particular embodiment, preferably m=n.

In addition to a complex or salt structure of the triazolyl-tetrazinyl-aminotriazine compound, a useful structure of the triazolyl-tetrazinyl-aminotriazine compound in pyrotechnic compositions includes $Z^+$ being $H^+$, t=1, m=1, n=1, and x=0. When $Z^+$ comprises $H^+$, and m and n are both equal to 1, the calculated heat of formation is approximately 255 kcal/mole (gas phase), and a density of approximately 1.77 g/cc (calcd) which provides significant energy to the pyrotechnic composition.

The $Z^+$ component of the triazolyl-tetrazinyl-aminotriazine compound preferably comprises a cation. As a salt, the compound may be selected from a large number and/or variety of cations as suitable for any particular pyrotechnic. Suitable cations of the present invention include those appropriate to provide color displays from combusting fireworks, particularly metals or amine salts. Metals of the present invention may include, without limitation sodium (Na), cobalt (Co), copper (Cu), aluminum (Al), nickel (Ni), barium (Ba), strontium (Sr), calcium (Ca), potassium (K), iron (Fe), titanium (Ti), magnesium (Mg), antimony (Sb) and the like. Additionally, typical amine salts may include compounds with $Z^+$ being, without limitation, $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, $C(NH_2)_3$, $(HONH_3)$, and bis(1(2)H-tetrazol-5-yl)-amine ($C_2H_4\ N_9$), the monohydrate of bis(1(2)H-tetrazol-5-yl)-amine ($C_2H_4N_9.H_2O$). Ignition or combustion of $Z^+$ of the present invention preferably results in a color, however, additional salts and other compositions maybe added in combination with the triazolyl-tetrazinyl-aminotriazine compounds to form the pyrotechnic compositions, as later described. Use of the metal salts of the triazolyl-tetrazinyl-aminotriazine compounds as colorants within the pyrotechnic compositions may generally include the metals conventionally used in pyrotechnic compositions. For example, strontium, barium, copper, and iron salts of triazolo-tetrazino-aminotriazine compounds, and salts thereof, can be expected to yield red, blue, green, yellow, purple, red-purple, and blue-green colorants.

The following structures exemplify non-limiting examples of possible salts for use in the pyrotechnic compositions of the present invention:

Examples 2 and 3
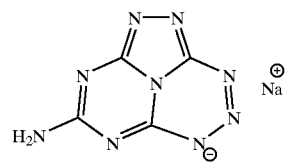

Example 4
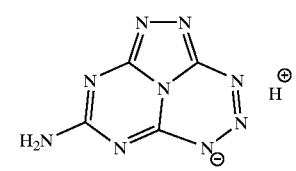

Example 5
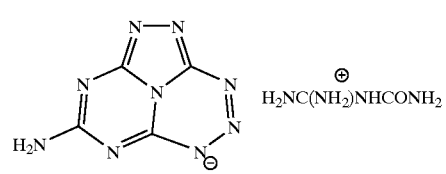

Example 6
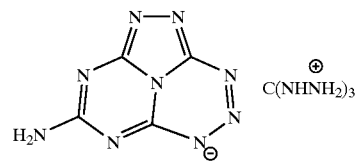

Example 7
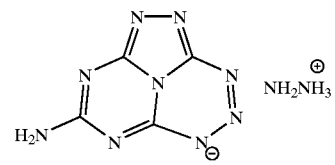

Example 8
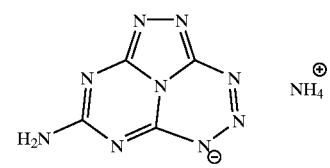

Example 9
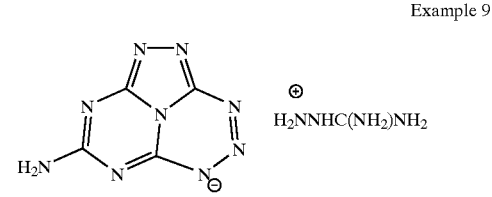

Example 10
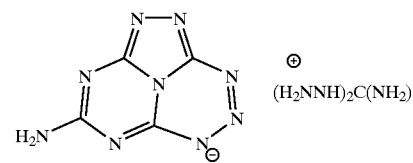

Example 11
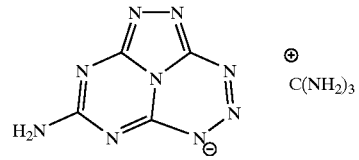

Example 12
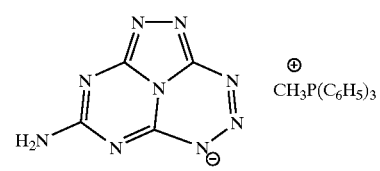

Example 13
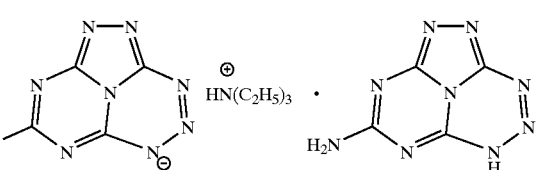

Example 14
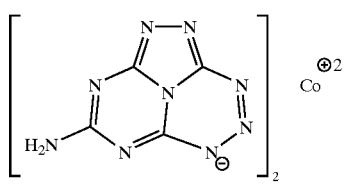

Example 15
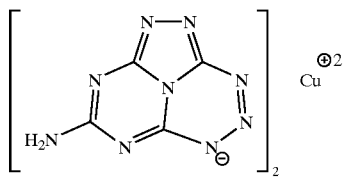

Example 16
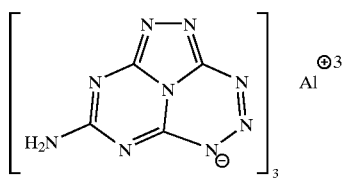

Example 17
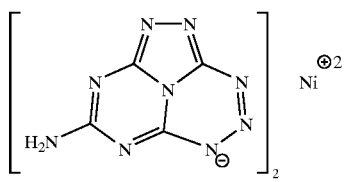

Example 18
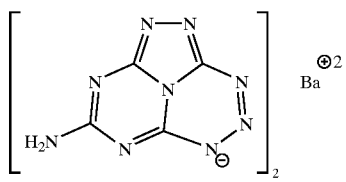

Example 20
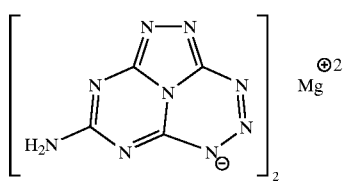

Example 19A
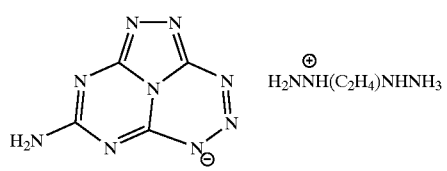

Example 19B
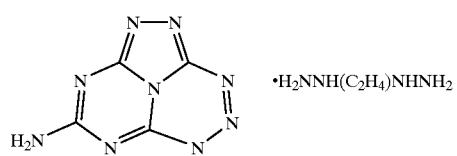

Example 21
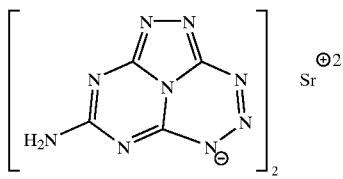

Example 22
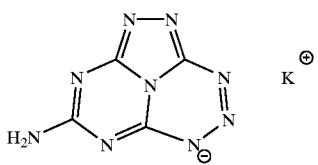

The pyrotechnic composition generally includes the addition of an oxidant to fully consume the carbon and hydrogen components of the pyrotechnic compositions during burning. Suitable oxidizers can generally include, without limitation, one or more alkaline earth metal nitrates, alkaline earth metal nitrites, alkali metal nitrates, alkali metal nitrites, transition metal oxides, such as ammonium perchlorate, alkali perchlorates such as potassium perchlorate and the like, ammonium nitrate, and alkali nitrates such as potassium nitrate and the like, or combinations thereof. Examples of the oxidizer include at least one of an alkali metal or an alkaline earth metal nitrate, a complex salt nitrate, such as $Ce(NH_4)_2 (NO_3)_6$ or $ZrO(NO_3)_2$, a dried, hydrated nitrate, such as $Ca(NO_3)_2 \cdot 4H_2O$ or $Cu(NO_3)_2 \cdot 2.5\ H_2O$, silver nitrate, an alkali or alkaline earth chlorate or perchlorate, ammonium perchlorate, a nitrite of sodium, potassium, or silver. Additionally, organic compositions such as a solid organic nitrate, nitrite, or amine, such as guanidine nitrate, nitroguanidine and 5-aminotetrazole maybe included. The oxidizer may include silver nitrate or a co-melt or mixture comprising silver nitrate and at least one of an alkali metal nitrate, an alkaline earth metal nitrate, a complex salt nitrate, a dried, hydrated nitrate, an alkali metal chlorate, an alkali metal perchlorate, an alkaline earth metal chlorate, an alkaline earth metal perchlorate, ammonium perchlorate, sodium nitrite, potassium nitrite, silver nitrite, or a complex salt nitrite; and independently a solid organic nitrate, a solid organic nitrite, or a solid organic amine. Alkali chlorates are generally not preferred as oxidizer due to sensitivity concerns. Ammonium perchlorate and ammonium nitrate are preferred oxidizers as the absence of any metal ions is better for control of the fireworks color and eliminates any ash residue. Ammonium perchlorate is particularly preferred as the oxidizer to provide a source of chlorine ions to the pyrotechnic composition. Chlorine ion may be supplied by addition of a metal chloride salt as the colorant or by use of ammonium perchlorate as the oxidizer, or a part thereof. Ammonium nitrate is hygroscopic and compositions including ammonium nitrate must be protected from moisture. The oxidizer is generally added with the triazolyl-tetrazinyl-aminotriazine compounds, or their complexes or salts, in amounts sufficient to provide about three equivalents of free oxygen. For example, the ammonium perchlorate oxidizes the triazolyl-tetrazinyl-aminotriazine anion to carbon dioxide and water if in a ratio of two parts by weight ammonium perchlorate to one part of the organic anion. The same degree of oxidation requires four parts ammonium nitrate.

Generally, the compositions can include from about 30 percent by weight to about 60 percent by weight of the high-nitrogen content, low-carbon content energetic material, more preferably from about 35 percent by weight to about 55 percent by weight, together with about 40 to about 60 percent by weight of the selected oxidizer.

As previously described, the pyrotechnic may further include a colorant in addition to the triazolyl-tetrazinyl-aminotriazine complex or salt. Colorants may be additional metal salts, or other compositions, as known in the art. For example, each metal salt has an anticipated colorant effect within a pyrotechnic composition, as each metal has well-known spectra associated with the burning of that metal. These include strontium salts such as strontium nitrate ($Sr(NO_3)_2$) or strontium carbonate ($SrCO_3$) for the color red, calcium salts such as calcium carbonate for the color red-orange, barium salts such as barium nitrate ($Ba(NO_3)_2$), barium chlorate ($Ba(ClO_3)_2$) or boron compounds for the color green, sodium salts such as sodium nitrate for the color orange-yellow, or sodium oxalate ($Na_2C_2O_4$) or cryolite ($3NaF.AlF_3$) for yellow, copper salts such as copper oxide, $CuCO_3$, Paris Green [$CuAs_2O_4.Cu(Ac)_2$] for the color blue, potassium salts such as potassium chloride for the color purple or violet, and magnesium, aluminum, antimony salts such as antimony sulfide ($Sb_2S_3$) for the color white. Combinations of these and other metal salts may be used to provide additional colors, such as orange from a combination of calcium carbonate and sodium nitrate, red-purple from a combination of copper sulfide and strontium nitrate, and yellow from a combination of barium nitrate and sodium nitrate. Other metal salts such as cadmium, uranium, gold, mercury, arsenic, iron and lead may be used to provide other colors if desired, although many such salts are not generally preferred due to toxicity. Nitrate salts are generally more preferred than chloride salts as chloride salts tend to occur as hydrates and thus contribute undesired water. The colorant is generally added in amounts from about 0.5 percent by weight to about 20 percent by weight, preferably from about 1 percent by weight to about 10 percent by weight based on the total weight of fuel, oxidant and colorant. These additional salts may include metal salts of calcium, titanium, aluminum, magnesium, and the like. Metal flakes or particles may be added to the pyrotechnic compositions to provide a glitter effect. Suitable metals can include aluminum, magnesium, titanium and iron. Iron can generally be added in the form of steel shavings to avoid rusting problems from moisture.

One preferred pyrotechnic formulation includes a triazolyl-tetrazinyl-aminotriazine compound together with two parts ammonium perchlorate as the oxidizer for complete oxidation, with from about 10 percent by weight of a colorant. It is most preferred that the triazolyl-tetrazinyl-aminotriazine compound comprises a salt of cobalt or copper.

The pyrotechnic composition is formed from mixing or packing the triazolyl-tetrazinyl-aminotriazine compound, including its salt or complex, in an appropriate delivery combination for use as fireworks, with the appropriate mixing and packing being within the capabilities of a person of ordinary skill in the art of manufacturing fireworks. The triazolyl-tetrazinyl-aminotriazine compound is diazotized from the triazolyl-triaminotriazine precursor, as taught herein, to form the appropriate pyrotechnic salt. Diazotization occurs by reacting the triazolyl-triaminotriazine precursor with a nitrite salt, such as, without limitation, nitric oxide, sodium nitrite, potassium nitrite and the like. The triazolyl-triaminotriazine precursor(s), including the acid salts thereof, are diazotized in an appropriate aqueous acid, such as for example hydrochloric or sulfuric acid, with the nitrite salt to give the ring-closed tetrazine product of the triazolyl-tetrazinyl-aminotriazine compound. The use of sodium nitrite (Z=Na) to form the triazolyl-tetrazinyl-aminotriazine compound is preferred. The triazolyl-tetrazinyl-aminotriazine compound (Z=Na) can be acidified to produce the parent acid of the triazolyl-tetrazinyl-aminotriazine compound (i.e., Z=H). Other triazolyl-tetrazinyl-aminotriazine compounds may be formed by neutralization of the parent acid or by cation exchange reactions with the sodium salt.

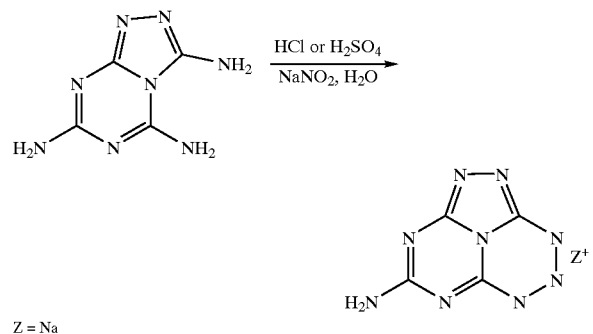

The preparation of triazolyl-tetrazinyl-aminotriazine salts by neutralization of the parent acid (Method A) occurs by reaction with amine bases or by reaction with metal hydroxides. Cation exchange with the sodium salt to form the triazolyl-tetrazinyl-aminotriazine salts (Method B) occurs by the process that includes an aqueous solution of the sodium salt being mixed with a solution of barium nitrate, strontium nitrate, calcium nitrate, or other.

Precursor

The precursor comprises a 1,2,4-triazolo[4,3-a][1,3,5]triazine-3,5,7-triamine, acid salt or its neutralized form of 1,2,4-triazolo[4,3-a][1,3,5]triazine-3,5,7-triamine. The general process involves ring closure of 2,4-diamino-6-hydrazino-s-triazine with an acid and a chemical of the general formula RCN where the R comprises a leaving group, and then neutralizing the acid.

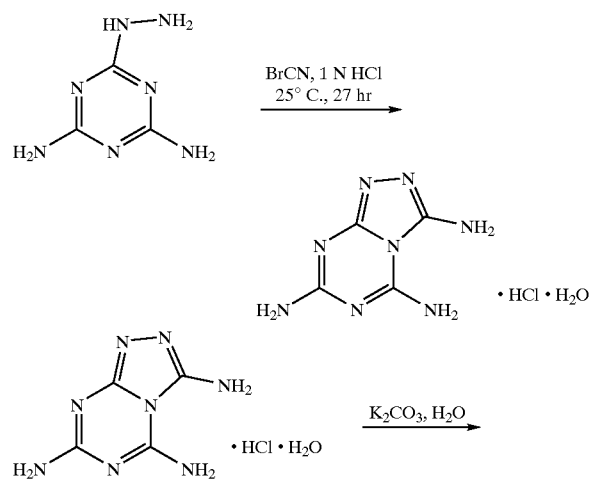

-continued

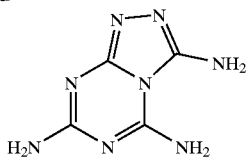

The structure of the precursor is shown below:

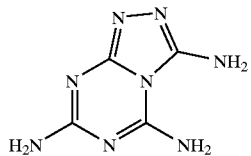

More specifically, the 1,2,4-triazolo[4,3-a][1,3,5]triazine-3,5,7-triamine, acid salt is derived first by obtaining or synthesizing 2,4-diamino-6-hydrazino-s-triazine. One method for synthesizing this chemical is set forth in U.S. Pat. No. 3,061,605 by D'Alelio. The general method is to effect a reaction between 2,4-diamino-6-chloro-1,3,5-triazine and hydrazine. A specific example is set forth in column 3, lines 60–70 of the above patent which is hereby incorporated by reference. While this particular method of synthesizing 2,4-diamino-6-hydrazino-s-triazine is specifically disclosed, any prior art method of synthesis would be appropriate to practice the present invention. The 2,4-diamino-6-hydrazino-s-triazine is dissolved with an acid, preferably out at room temperature with an acid that is of sufficient strength to dissolve the 2,4-diamino-6-hydrazino-s-triazine. Many acids can be employed in the present invention, such as sulfuric acid or hydrochloric acid or mixtures of these acids with other solvents such as methanol or ethanol, and may be selected by one skilled in the art. One preferred acid is 1N hydrochloric acid. The dissolved 2,4-diamino-6-hydrazino-s-triazine is mixed with a reagent of the formula RCN, wherein R comprises a leaving group. This reaction will provide the amino triazole ring on the product directly. A leaving group, as used in this application, is a group that can be displaced to give ring closure; that is, produces the amino triazole ring. One preferred leaving group comprises bromine wherein the reagent comprises cyanogen bromide. Although the reaction in this step is acid catalyzed, preferred reaction times range from about twenty hours to about thirty hours in order to allow for the maximum formation of acid salt crystals. It is also preferred that the acid salt crystals be removed after the reaction is substantially complete, approximately thirty hours, to prohibit contamination of the final product with impurities. The crystals may be removed by any normal method, such as filtration, and can then be washed and dried in order to obtain the final acid salt product.

Neutralization of the 1,2,4-triazolo[4,3-a][1,3,5]triazine-3,5,7-triamine, acid salt crystals synthesized above to obtain a final product of 1,2,4-triazolo[4,3-a][1,3,5]triazine-3,5,7-triamine is accomplished by mixing the crystals with a substance more basic than 1,2,4-triazolo[4,3-a][1,3,5]triazine-3,5,7-triamine. This step results in the removal of the acid from the above reaction and provides for a final product of 1,2,4-triazolo[4,3-a][1,3,5]triazine-3,5,7-triamine. The substance used in this final step may be selected by one skilled in the art based upon the basicity of the substance versus the basicity of 1,2,4-triazolo[4,3-a][1,3,5]triazine-3,5,7-triamine. Some examples are potassium carbonate, potassium acetate, sodium bicarbonate, and sodium hydroxide. One preferred substance is potassium carbonate. It is also preferred that the reaction take place in solution, so preferably, water or some other solvent may be added to the salt.

The following examples (Examples 1A-1C) are preparations of the 1,2,4-triazolo[4,3-a][1,3,5]triazine-3,5,7-triamine precursors:

EXAMPLE 1A

Preparation of 1,2,4-triazolo[4,3-a][1,3,5]triazine-3,5,7-triamine, Hydrochloric Salt Hydrate To 126 g of 1 N hydrochloric acid stirred at 25° C. was added 9.06 g (0.0570 mole) of 2,4-diamino-6-hydrazino-s-triazine [prepared according to G. F. D'alelio, U.S. Pat. No. 3,061,605 (1962), which is incorporated herein by reference]. The mixture was stirred for 10 minutes, at which time nearly all of the 2,4-diamino-6-hydrazino-s-triazine had dissolved. Cyanogen bromide (9.3 g, 0.0877 mole) was added at one time and, after 5 minutes, all of the material was in solution. After about 1 hour, crystals began to precipitate. After 3 hours, stirring was stopped and the mixture was allowed to stand for an additional 24 hours to continue precipitation of crystals. The crystals were removed by filtration and washed with 2×25 ml cold water. The crystals were air dried and then dried in a vacuum desiccator over Drierite to give 8.60 g (68.4% yield) of product. IR (KBr): 3300, 3155, 1708, 1695, 1624, 1534, 1490, 1444, 1339, 1173, 1073, 979, 845, 772 cm$^{-1}$. Anal. Calcd for $C_4H_6N_8$ (HCl)($H_2O$): C, 21.77; H, 4.11; N, 50.79; Cl, 16.07. Found: C, 21.84; H, 4.25; N, 50.02; Cl, 16.02

EXAMPLE 1B

Preparation of 1,2,4-triazolo[4,3-a][1,3,5]triazine-3,5,7-triamine

To 6.86 g (0.031 mole) of 1,2,4-triazolo[4,3-a][1,3,5]triazine-3,5,7-triamine, hydrochloric salt hydrate stirred in 175 ml of water was added 4.40 g (0.031 mole) of potassium carbonate and the mixture was stirred vigorously for 40 minutes. The solid was removed by filtration, washed with water, and dried to give 4.83 g (94%) of 1,2,4-triazolo[4,3-a][1,3,5]triazine-3,5,7-triamine. $^{13}$C NMR ($CD_3CO_2D/D_2O$, 1:1 by vol): 145.7, 151.1, 151.9, 164.0. $^{13}$C NMR($D_2SO_4$): 133.6, 141.9, 143.1, 149.5. IR(KBr): 3413, 3314, 3096, 1654, 1611, 1540, 1480, 1430, 1375, 979, 859, 770 cm$^{-1}$. Anal. Calcd for $C_4H_6N_8$: C, 28.92; H, 3.64; N, 67.44. Found: C, 28.64; H, 3.65; N, 66.08.

EXAMPLE 1C

Preparation of 1,2,4-triazolo[4,3-a][1,3,5]triazine-3,5,7-triamine, Hydrochloric Salt Hydrate To 0.31 g (0.003 mole) of 37% hydrochloric acid in water (4 ml) and methanol (21 ml) stirred at 25° C. was added 0.42 g (0.003 mole) of 2,4-diamino-6-hydrazino-s-triazine [prepared according to G. F. D'alelio, U.S. Pat. No. 3,061,605 (1962)]. Cyanogen bromide (0.32 g, 0.003 mole) was then added at one time. The solution was held at 77–80° C. for 3 hours, before it was cooled to 25° C. and a small amount of solid was removed by filtration. The volatiles were removed from the filtrate to give 0.60 g of solid that was mainly 1,2,4-triazolo[4,3-a][1,3,5]triazine-3,5,7-triamine, hydrochloric salt hydrate by TLC and IR analyses.

Examples 1A and 1C

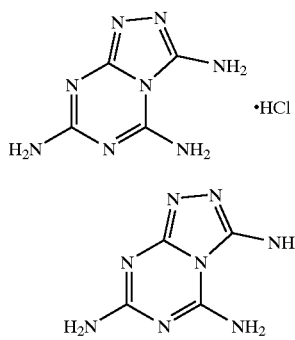

Example 1B

The following examples (Examples 2–18) are preparations of the triazolyl-tetrazinyl-aminotriazine compounds:

EXAMPLE 2

Preparation of triazolyl-tetrazinyl-aminotriazine, Sodium Salt (Z=Na)

1,2,4-triazolo[4,3-a][1,3,5]triazine-3,5,7-triamine, hydrochloric acid salt hydrate (4.20 g, 0.0190 mole) was added to aqueous hydrochloric acid stirred in an ice bath to produce a slurry [The aqueous hydrochloric acid was prepared by adding 8.0 g of 37% concentrated HCl (0.08 mole HCl) to 75 ml of water]. The ice-cold slurry was added in seven portions over approximately 15 minutes to a solution of 16.5 g (0.24 mole) of sodium nitrite in 50 ml of water stirred in an ice bath. Stirring in the ice bath was continued for two hours before the yellow mixture was allowed to warm to 20° C. over approximately one hour. The mixture was heated to 60° C. over 30 minutes and then held at 60–65° C. for one hour. The hot mixture was filtered to remove an insoluble brown solid, after which the filtrate was cooled to 5° C. to give 2.16 g of red crystals. Concentration of the aqueous mother liquor under reduced pressure gave an additional 0.73 g of product to bring the total yield to 2.89 g (70%), mp>300° C. (gradual decomp. with loss of red color above 220° C.). The product contains a small amount of a by-product (nitrotriazolo-diaminotriazine) which can be removed by filtration when the product is dissolved in warm water. Analysis showed: $^1$H NMR (DMSO-$d_6$): 6.67 (s). $^{13}$C NMR (DMSO-$d_6$): 146.1, 151.7, 153.1, 167.7. Anal. Calcd for $C_4H_2N_9Na(H_2O)$: C, 22.13; H, 1.86; N, 58.06, Na, 10.59. Found: C, 22.04; H, 1.93; N, 57.35, Na, 11.00.

EXAMPLE 3

Preparation of triazolyl-tetrazinyl-aminotriazine, Sodium Salt (from triazolo-triaminotriazole)

An ice cold slurry of 0.63 g (0.0038 mole) of 1,2,4-triazolo[4,3-a][1,3,5]triazine-3,5,7-triamine in 15 ml of aqueous sulfuric acid (containing 1.0 g, 0.01 mole $H_2SO_4$) was added in 1.5 ml portions over 5 minutes to a solution of 3.3 g (0.048 mole) of sodium nitrite in 10 ml of water stirred in an ice bath. The mixture was stirred at ice bath temperature for 2.5 hours before it was held at 20° C. for 10 minutes and then at 50–53° C. for 45 minutes. The warm mixture was filtered to remove an insoluble brown solid and the filtrate was held at 80–85° C. for 15 minutes. The red solution was allowed to stand at room temperature to precipitate red crystals (0.33 g). Concentration of the mother liquor gave additional product, raising the total to 0.43 g (52%).

EXAMPLE 4

Preparation of triazolyl-tetrazinyl-aminotriazine, (Parent Acid) (Z=H)

Triazolyl-tetrazinyl-aminotriazine, sodium salt hydrate (2.9 g, 0.0134 mole) was dissolved in 70 ml of warm water. The solution was stirred at 25° C. while adding dropwise 15 ml of 1N aqueous hydrochloric acid. The yellow precipitate that formed was removed by filtration and washed with cold water to give 1.9 g (81%) of yellow solid, mp 215° C., rapid decomposition. Analysis showed: $^1$H NMR (DMSO-$d_6$): 13.65 (very broad signal, 1H), 8.06, 7.96 (d, 2H). $^{13}$C NMR (DMSO-$d_6$): 143.9 (1C), 149.6 (2C), 167.5 (1C).

EXAMPLES 5 through 18 describe the preparation of additional salts of triazolyl-tetrazinyl-aminotriazine either by neutralization of the parent acid (Method A) or by cation exchange with the sodium salt (Method B).

EXAMPLE 5

Preparation of triazolyl-tetrazinyl-aminotriazine, Guanyl Urea Salt (Z=$H_2NC(NH_2)NHCONH_2$) via Neutralization of the Parent Acid (Method A):

A solution of 0.15 g (0.5 mmole) of N-guanyl urea sulfate hydrate, $[H_2NC(NH_2)NHCONH_2]_2H_2SO_4xH_2O$, in 3 ml of water was neutralized with 1 ml of aqueous sodium hydroxide (containing 0.04 g, 1 mmole of NaOH). This solution (containing N-guanyl urea as a free base) was added dropwise to a stirred suspension of the parent acid (triazolo-tetrazino-aminotriazine) in 3 ml of water. The mixture was stirred for 2 hours at 25° C., then was cooled to 5° C., and the insoluble product was removed by filtration and washed with cold water to give 0.24 g (96%) of red solid, mp>300° C. (gradual decomp. with loss of red color above 240° C.). Analysis showed: $^1$H NMR (DMSO-$d_6$): 6.73 (s, 2H) 7.09 (broad signal, 2H), 8.04 (very broad signal, 4H). $^{13}$C NMR (DMSO-$d_6$): 146.1, 151.7, 153.1, 154.6, 155.2, 167.7. Anal. Calcd for $C_6H_9N_{13}O$ ($H_2O$): C, 24.24; H, 3.73; N, 61.26. Found: C, 24.19; H, 3.68; N, 60.71. X-ray crystal structure analysis also confirmed the structure of the product to be triazolyl-tetrazinyl-aminotriazine, guanyl urea salt hydrate.

EXAMPLE 6

Preparation of triazolyl-tetrazinyl-aminotriazine, Triaminoguanidine Salt [Z=$C(NHNH_2)_3$] via Cation Exchange (Method B)

A solution of triazolyl-tetrazinyl-aminotriazine, sodium salt hydrate (0.32 g, 1.45 mmole) in 10 ml of water was stirred at 25° C. while triaminoguanidinium nitrate (0.25 g, 1.50 mmole) was added in three portions over one minute. After a short time, red crystals began to precipitate from the solution. The mixture was stirred at 25° C. for two hours before it was cooled to 5° C. and filtered to give 0.25 g of red crystals. Additional product from concentration of the filtrate raised the total yield to 0.29 g (71%), mp 195° C., rapid dec. Recrystallization from water raised the mp to 203° C., rapid dec. Analysis showed: $^1$H NMR (DMSO-$d_6$): 4.48 (s, 6H), 6.65 (s, 2H), 8.59 (s, 3H). $^{13}$C NMR (DMSO-$d_6$): 146.1, 151.7, 153.1, 158.9, 167.7. Anal. Calcd for $C_5H_{11}N_{15}$ ($H_2O$): C, 20.07; H, 4.38; N, 70.21. Found: C, 20.22; H, 4.30; N, 69.64.

EXAMPLE 7

Preparation of triazolyl-tetrazinyl-aminotriazine, Hydrazinium Salt [Z=$NH_2NH_3$]

Via Method A: The parent acid was neutralized with one equivalent of aqueous hydrazine to give red crystals (74%), mp 200° C., rapid dec. Analysis showed: $^1$H NMR (DMSO-$d_6$): 6.68 (s)(merged with a broad s at 7.05). $^{13}$C NMR (DMSO-$d_6$): 146.1, 151.7, 153.1, 167.7. Anal. Calcd for $C_4H_7N_{11}$: C, 22.96; H, 3.38; N, 73.66. Found: C, 23.06; H, 3.51; N, 71.56.

EXAMPLE 8

Preparation of triazolyl-tetrazinyl-aminotriazine, Ammonium Salt [Z=NH$_4$]

Via Method A: The parent acid was neutralized in water with one equivalent of aqueous ammonia to give red crystals (74%), mp>300° C. (with gradual decomp and loss of red color above 220° C.). Analysis showed: $^1$H NMR(DMSO-$d_6$): 6.69(s) 7.12 (bs). $^{13}$C NMR(DMSO-$d_6$): 146.1, 151.7, 153.1, 167.7. Anal. Calcd for $C_4H_6N_{10}$: C, 24.74; H, 3.12; N, 72.14. Found: C, 24.40; H, 3.04; N, 70.23.

EXAMPLE 9

Preparation of triazolyl-tetrazinyl-aminotriazine, Aminoguanidinium Salt [Z=H$_2$NNHC(NH$_2$)NH$_2$]

Via Method A: The parent acid was neutralized in water with aminoguanidine bicarbonate [H$_2$NNHC(=NH)NH$_2$ (H$_2$CO$_3$)] using equal molar amounts to give red crystals (81%), mp 227° C., dec. Analysis showed: $^1$H NMR (DMSO-$d_6$): 4.68 (s, 2H), 6.67 (s, 2H), 6.76, 7.23 (two bs, 4H), 8.58 (s, 1H). $^{13}$C NMR (DMSO-$d_6$): 146.1, 151.7, 153.1, 158.5, 167.7. Anal. Calcd for $C_5H_9N_{13}$: C, 23.90; H, 3.61; N, 72.48. Found: C, 23.65; H, 3.65; N, 70.91.

EXAMPLE 10

Preparation of triazolyl-tetrazinyl-aminotriazine, Diaminoguanidinium Salt [Z=(H$_2$NNH)$_2$C(NH$_2$)]

Via Method B: The sodium salt hydrate and diaminoguanidinium hydrochloride were combined in equimolar amounts in water to give a precipitate of red crystals (71%), mp 196° C., dec. Recrystallization from water gave mp 199° C., dec. Analysis showed: $^1$H NMR (DMSO-$d_6$): 4.59 (s, 4H), 6.68 (s, 2H), 7.16 (s, 2H), 8.58 (s, 2H). $^{13}$C NMR (DMSO-$d_6$): 146.1, 151.7, 153.1, 159.7, 167.7. Anal. Calcd for $C_5H_{10}N_{14}$: C, 22.56; H, 3.79; N, 73.66. Found: C, 22.52; H, 3.89; N, 71.88.

EXAMPLE 11

Preparation of triazolyl-tetrazinyl-aminotriazine, Guanidinium Salt [Z=C(NH$_2$)$_3$]

Via Method B: The sodium salt hydrate and guanidinium hydrochloride were combined in equimolar amounts in water to give a precipitate of red crystals (73%), mp 263° C., dec. Analysis showed: $^1$H NMR (DMSO-$d_6$): 6.69 (s, 2H), 6.95(s, 6H). $^{13}$C NMR (DMSO-$d_6$): 146.1, 151.7, 153.1, 157.6, 167.7. Anal. Calcd for $C_5H_8N_{12}$(H$_2$O): C, 23.62; H, 3.96; N, 66.12. Found: C, 23.53; H, 3.96; N, 64.12.

EXAMPLE 12

Preparation of triazolyl-tetrazinyl-aminotriazine, Methyltriphenylphosphonium Salt [Z=CH$_3$P(C$_6$H$_5$)$_3$]

Via Method B; The sodium salt hydrate and methyltriphenylphosphonium bromide were combined in equimolar amounts in water to give a precipitate of red crystals, mp 69–72° C. Analysis showed: $^1$H NMR (DMSO-$d_6$): 3.10, 3.17 (pair of s, 3H), 6.66 (s, 2H), 7.72–7.88 (m, 15H). $^{13}$C NMR (DMSO-$d_6$): 118.9, 120.7, 129.9, 130.1, 133.0, 133.2, 134.86, 134.74, 146.1, 151.7, 153.1, 167.7.

EXAMPLE 13

Preparation of triazolyl-tetrazinyl-aminotriazine, Triethylamine Salt [Z=HN(C$_2$H$_5$)$_3$]

Via Method A: The parent acid was treated with an equimolar amount of triethylamine in methanol. The solvent was partially removed under reduced pressure to give red crystals, mp 205° C., dec. The product is the triethylamine salt, which has separated from solution in the form of a complex with an additional molecule of the parent acid. Analysis showed: $^1$H NMR (DMSO-$d_6$): 1.17 (t, 9H), 3.10 (q, 6H), 3.82 (very broad s), 7.33 (broad s, 3H). $^{13}$C NMR (DMSO-$d_6$): 8.4, 45.6, 145.1, 150.7, 151.4, 167.6. Anal. Calcd for $C_{10}H_{18}N_{10}$(C$_4$H$_3$N$_9$): C, 36.92; H, 4.65; N, 58.43, Found: C, 36.54; H, 4.73; N, 57.56.

EXAMPLE 14

Preparation of triazolyl-tetrazinyl-aminotriazine, Cobalt Salt [Cation=Co(II)]

Via Method B: The sodium salt hydrate and a water soluble cobalt (II) salt (e.g. cobalt (II) perchlorate hexahydrate or cobalt (II) nitrate hexahydrate) are combined in water to give a precipitate of red-orange crystals [Co(C$_4$H$_2$N$_9$)$_2$(6 H$_2$O)](89%). Analysis showed: Anal. Calcd for $C_8H_4N_{18}$Co (6 H$_2$O): C, 18.50; H, 3.11; N, 48.55; Co, 11.35. Found: C, 18.45; H, 3.22; N, 48.24; Co, 11.27.

EXAMPLE 15

Preparation of triazolyl-tetrazinyl-aminotriazine, Copper Salt [Cation=Cu(II)]

Via Method B: The sodium salt hydrate and a water soluble copper (I) salt (e.g. copper (II) perchlorate hexahydrate or copper (II) nitrate hemipentahydrate) are combined in water to give a precipitate of red-orange crystals [Cu(C$_4$H$_2$N$_9$)$_2$ (5 H$_2$O)] (92%). Anal. Calcd for $C_8H_4N_{18}$Cu (5 H$_2$O): C, 18.99; H, 2.79; N, 49.84; Cu, 12.56. Found: C, 18.99; H, 2.84; N, 49.48; Cu, 12.88.

EXAMPLE 16

Preparation of triazolyl-tetrazinyl-aminotriazine, Aluminum Salt [Cation=Al(III)]

Via Method B: The sodium salt hydrate and a water soluble aluminum (III) salt (e.g. aluminum (III) perchlorate nonahydrate or aluminum (III) nitrate nonahydrate) are combined in water to give a precipitate of orange crystals [Al(C$_4$H$_2$N$_9$)$_3$(7.5 H$_2$O)] (78%). Analysis showed: 1H NMR (DMSO-$d_6$): 7.61, 7.68 (d). $^{13}$C NMR (DMSO-$d_6$): 144.5, 150.2, 150.5, 167.6. Anal. Calcd for $C_{12}H_6N_{27}$Al (7.5 H$_2$O): C, 20.87; H, 3.07; N, 54.77; Al, 3.91. Found: C, 21.24; H, 3.23; N, 54.53; Al, 3.38.

EXAMPLE 17

Preparation of triazolyl-tetrazinyl-aminotriazine, Nickel Salt [Cation=Ni(II)]

Via Method B: The sodium salt hydrate and a water soluble nickel (II) salt (e.g. nickel (II) perchlorate hexahydrate or nickel (II) nitrate hexahydrate) are combined in water to give a precipitate of orange crystals [Ni(C$_4$H$_2$N$_9$)$_2$(xH$_2$O)] (92% for x=6). Anal. Calcd for C$_8$H$_4$N$_{18}$Ni (6 H$_2$O): C, 18.51; H, 3.11; N, 48.57; Ni, 11.31. Found: C, 18.57; H, 2.82; N, 47.85; Ni, 11.87.

EXAMPLE 18

Preparation of triazolyl-tetrazinyl-aminotriazine, Barium Salt [Cation=Ba(II)]

Via Method B: The sodium salt hydrate and a water soluble barium (II) salt (e.g. barium (II) perchlorate xH2O or barium (II) nitrate) are combined in water to give a precipitate of red crystals [Ba(C$_4$H$_2$N$_9$)$_2$ (xH$_2$O)] (87% for x=6). Analysis showed: $^1$H NMR (DMSO-d6): 6.66 (s). $^{13}$C NMR (DMSO-d6): 146.1, 151.8, 153.2, 167.7. For [Ba(C$_4$H$_2$N$_9$)$_2$(7H$_2$O)] (85%); analysis showed $^1$H NMR (DMSO-d$_6$): 6.66 (s). $^{13}$C NMR (DMSO-d$_6$): 146.1, 151.8, 153.2, 167.7. Anal. Calcd for C$_8$H$_4$N$_{18}$Ba (7 H$_2$O): C, 15.60; H, 2.95; N, 40.95; Ba, 22.31. Found: C, 15.22; H, 3.13; N, 39.14; Ba, 22.16.

A sample of the red crystals [Ba(C$_4$H$_2$N$_9$)$_2$(7H$_2$O)] was dried at 100° C. for 43 hours.

Elemental analysis showed the crystals had lost water to yield [Ba(C$_4$H$_2$N$_9$)$_2$(2H$_2$O)]. Anal. Calcd for C$_8$H$_4$N$_{18}$Ba (2 H$_2$O): C, 18.28; H, 1.53; N, 47.97; Ba, 26.13. Found: C, 18.41; H, 1.92; N, 46.31; Ba, 25.68.

EXAMPLE 19

Preparation of triazolo-tetrazino-aminotriazine, 3,6-dihydrazino-1,2,4,5-Tetrazine Salt [Z=H$_2$NNH(C$_2$N$_4$)NHNH$_3$]

Via Method A: The parent acid was stirred in methanol/water with an equimolar amount of 3,6-dihydrazino-1,2,4,5-tetrazine (DHT) for 5 hours. The mixture was filtered to remove the rust colored solid, mp 165° C., very rapid dec. [For comparison, the dec. points of DHT and the parent acid are 155° C. and 215° C., respectively]. $^1$H NMR (DMSO-d$_6$): 3.0–7.0 (various broad absorptions), 7.76, 7.69 (d), 8.52 (s). $^{13}$C NMR (DMSO-d$_6$): 144.4, 149.7, 150.6 (broadened), 162.4, 163.2, 167.7. For comparison spectra, DHT shows $^1$H NMR(DMSO-d$_6$): 4.25 (s, 4H), 8.38 (s, 2H)) and $^{13}$C NMR (DMSO-d$_6$): 163.3. The NMR spectra of the parent acid are given in example 4 above.

EXAMPLE 20

Preparation of triazolo-tetrazino-aminotriazine, Magnesium Salt [Cation=Mg(II)]

Via Method B: The sodium salt hydrate and a water soluble magnesium (II) salt (e.g. magnesium (1) perchlorate hexahydrate) are combined in water to give a precipitate of red crystals [Mg(C$_4$H$_2$N$_9$)$_2$(6H$_2$O)] (96%). Anal. Calcd for C$_8$H$_4$N$_{18}$Mg (6 H$_2$O); C, 19.83; H, 3.33; N, 52.02; Mg, 5.01. Found: C, 19.85; H, 3.44; N, 51.72; Mg, 5.15. $^1$H NMR (DMSO-d$_6$): 6.66 (s). $^{13}$C NMR(DMSO-d$_6$): 146.1, 151.8, 153.2, 167.7.

EXAMPLE 21

Preparation of triazolo-tetrazino-aminotriazine, Strontium Salt [Cation=Sr(II)]

Via Method B: The sodium salt hydrate and a water soluble strontium (II) salt (e.g. strontium (II) nitrate) are combined in water to give a precipitate of red-orange crystals [Sr(C$_4$H$_2$N$_9$)$_2$ (8H$_2$O)] (83%). Anal. Calcd for C$_8$H$_4$N$_{18}$Sr(8 H$_2$O); C, 16.45; H, 3.45; N, 43.17; Sr, 15.00. Found: C, 16.18; H, 3.65; N, 41.84; Sr, 14.79. $^1$H NMR (DMSO-d$_6$): 6.65 (s). $^{13}$C NMR (DMSO-d$_6$): 146.1, 151.8, 153.2, 167.7.

EXAMPLE 22

Preparation of triazolo-tetrazino-aminotriazine, Potassium Salt [Cation=K]

Via Method A: A suspension of the parent acid in water was well-stirred while a dilute aqueous solution containing an equivalent amount of potassium hydroxide (85% KOH) was added dropwise. The solution was filtered and the volatiles were removed from the filtrate under reduced pressure. The residue was washed with acetone and re-crystallized by dissolving in a minimum amount of water and adding acetone. The red crystals weighed 0.34 g after air-drying. The sample was then dried in a vacuum desiccator over Drierite for 24 hours to give 0.27 g [KC$_4$H$_2$N$_9$] (82%). Anal. Calcd for C$_4$H$_2$N$_9$K: C, 22.32; H, 0.94; N, 58.57; K, 18.17. Found: C, 21.94; H, 1.22; N, 56.61; K, 17.18. $^1$H NMR (DMSO-d$_6$): 6.66 (s). $^{13}$C NMR (DMSO-d$_6$): 146.1, 151.8, 153.2, 167.7.

The triazolyl-tetrazinyl-aminotriazine compounds of the pyrotechnic compositions of the present invention are high-nitrogen heterocyclic compounds that are particularly useful energetic ingredients for pyrotechnics because of their thermal stability, insensitivity, and their capability to moderate flame temperatures and propellant burn rates. They also provide efficient heating of the colorant metal cation, since it is part of the crystal structure of the high-energy, high-nitrogen compound. The trtiazolyl-tetrazinyl-aminotriazine compounds also provide a platform for a very large number of specialized salts useful in the pyrotechnic field, including those of metals, amines, or other cations. The pyrotechnic compositions of the present invention can be arranged into any appropriate fireworks display as determinable by those skilled in the art in light of the disclosure herein. Typical fireworks configuration include roman candle, single or multiple shells, bursts or flares and other such effects as are commonly used in the fireworks industry. These fireworks may be stationary or catapulted into the air, such as by use of a lifting charge, and include other necessary pyrotechnic components, including for example, colorants, oxidizer, black powder, bursting charge and other secondary charges, and fusing. It is particularly preferred that the pyrotechnic compositions of the present invention produce a minimal amount of smoke as to be useful not only in outdoor fireworks displays, but also useful in enclosed or confined arenas, such as staged productions providing one or more visual points of reference for an audience, indoors including stadium use, or otherwise within confirmed or limited spaces such as for use in the production of special effects for the film industry.

The foregoing summary, description, and examples of the invention are not intended to be limiting, but are only exemplary of the inventive features which are defined in the claims.

What is claimed is:

1. A pyrotechnic composition comprising a compound having the chemical structure:

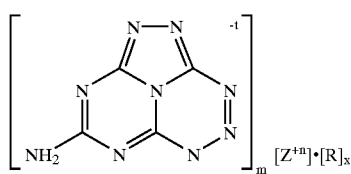

wherein $Z^+$ comprises $H^+$ or a cation; R comprises a complexing component; and, wherein m=1, 2 or 3; n=0, 1, 2 or 3; x=0, 1, 2 or 3; and t=0 or 1.

2. A pyrotechnic composition of claim 1, wherein $Z^+$ comprises $H^+$, R comprises a complexing component, and m=1, 2 or 3; n=1; and t=0 or 1.

3. A pyrotechnic composition of claim 1, wherein the compound comprises a salt with $Z^+$ comprising $H^+$ or a cation, and x=0, m=1, 2, or 3, n=1, 2, or 3, and m is equal to or less than n.

4. The pyrotechnic composition of claim 3, wherein m=n.

5. The compound of claim 3, wherein $Z^+$ comprises a cation.

6. The pyrotechnic composition of claim 3, wherein Z comprises a metal.

7. The pyrotechnic composition of claim 3, wherein Z comprises an amine salt.

8. The pyrotechnic composition of claim 3, wherein Z is selected from the group consisting of Na, Co, Cu, Al, Ni, Ba, Sr, $H_2NC(NH_2)NHCONH_2$, $C(NHNH_2)_3$, $NH_2NH_3$, $NH_4$, $H_2NNHC(NH_2)NH_2$, $(H_2NNH)_2C(NH_2)$, and $C(NH_2)_3$.

9. The compound of claim 6, wherein Z is selected from the group consisting of Na, Co, Cu, Al, Ni, Ba, and Sr.

10. The compound of claim 7, wherein Z is selected from the group consisting of $H_2NC(NH_2)NHCONH_2$, $C(NHNH_2)_3$, $NH_2NH_3$, $NH_3$, $H_2NNHC(NH_2)NH_2$, $(H_2NNH)_2C(NH_2)$, and $C(NH_2)_3$.

11. The pyrotechnic composition of claim 1, wherein combustion of $Z^+$ results in a color.

12. The pyrotechnic composition of claim 1, further comprising an oxidant.

13. The pyrotechnic composition of claim 12, wherein the oxidant is selected from the group consisting of ammonium perchlorate, ammonium nitrate, and combinations thereof.

14. The pyrotechnic composition of claim 1, further comprising a colorant.

15. The pyrotechnic composition of claim 14, wherein the colorant comprises a metal salt.

16. A method of making a pyrotechnic composition comprising a triazolyl-tetrazinyl-aminotriazine compound comprising the steps of:
providing a triazolo-triaminotriazine precursor; and,
diazotizing the precursor.

17. The method of claim 16, wherein the step of diazotizing the precursor comprises reacting the triazolo-triaminotriazine precursor with a nitrite salt.

18. The method of claim 17, wherein the nitrate salt is selected from the group consisting of sodium nitrate and potassium nitrate.

19. The triazolyl-tetrazinyl-aminotriazine formed by the process of claim 16.

20. A pyrotechnic composition comprising triazolyl-tetrazinyl-aminotriazine.

* * * * *